(12) United States Patent
Artsyukhovich et al.

(10) Patent No.: US 9,849,034 B2
(45) Date of Patent: Dec. 26, 2017

(54) RETINAL LASER SURGERY

(75) Inventors: Alexander Artsyukhovich, Irvine, CA (US); Mikhail Boukhny, Laguna Niguel, CA (US); Bruno Dacquay, Irvine, CA (US); Michael J. Yadlowsky, Sunnyvale, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1389 days.

(21) Appl. No.: 13/290,593

(22) Filed: Nov. 7, 2011

(65) Prior Publication Data
US 2013/0116670 A1 May 9, 2013

(51) Int. Cl.
*A61N 5/067* (2006.01)
*A61F 9/008* (2006.01)
*A61B 3/12* (2006.01)
*A61B 90/00* (2016.01)

(52) U.S. Cl.
CPC ........ *A61F 9/00821* (2013.01); *A61B 3/1233* (2013.01); *A61B 2090/373* (2016.02); *A61F 2009/00844* (2013.01); *A61F 2009/00863* (2013.01)

(58) Field of Classification Search
CPC ........ A61F 9/00821; A61F 2009/00863; A61F 2009/00844; A61B 2019/5231; A61B 3/1233
USPC .................................. 607/89; 606/4
See application file for complete search history.

(56) References Cited

U.S. PATENT DOCUMENTS

| | | |
|---|---|---|
| 3,747,019 A | 7/1973 | Koechner et al. |
| 4,476,519 A | 10/1984 | Hayamizu |
| 4,517,980 A | 5/1985 | Tagnon |
| 4,538,608 A | 9/1985 | L'Esperance, Jr. |
| 4,628,416 A | 12/1986 | Dewey |
| 4,676,594 A | 6/1987 | Presby |
| 4,686,992 A | 8/1987 | Dewey et al. |
| 4,718,417 A | 1/1988 | Kittrell et al. |
| 4,741,612 A | 5/1988 | Birngruber et al. |
| 4,758,081 A | 7/1988 | Barnes |

(Continued)

FOREIGN PATENT DOCUMENTS

| | | |
|---|---|---|
| EP | 0960609 | 1/1999 |
| EP | 2371327 | 10/2011 |

(Continued)

OTHER PUBLICATIONS

Goldberg, Leslie, "OptiMedica's Pattern Scan Laser System" (online), (retrieved from www.retinalphysician.com/printarticle. aspx?article=100246), Sep. 2006 (retrieved on Jul. 27, 2011) (2 pages).

(Continued)

*Primary Examiner* — Alyssa M Alter

(57) ABSTRACT

Various systems, processes, and computer program products may be used to perform retinal laser surgery. In particular implementations, systems, processes, and computer program products may include the ability to identify retina blood vessels from a retina image and determine a retina location needing therapy and not substantially intersecting a retina blood vessel. The systems, processes, and computer program products may also include the ability to generate a command to activate a retinal laser when a beam from the retinal laser will be aligned with the therapeutic location.

28 Claims, 5 Drawing Sheets

(56) References Cited

U.S. PATENT DOCUMENTS

| | | |
|---|---|---|
| 4,895,154 A | 1/1990 | Bartelt et al. |
| 4,901,718 A * | 2/1990 | Bille ............... A61B 18/20 606/18 |
| 4,934,787 A | 6/1990 | Ichimura et al. |
| 4,974,930 A | 12/1990 | Blyler, Jr. et al. |
| 5,171,242 A | 12/1992 | Dewey et al. |
| 5,207,673 A | 5/1993 | Ebling et al. |
| 5,260,953 A | 11/1993 | Rowe |
| 5,336,216 A | 8/1994 | Dewey |
| 5,342,351 A | 8/1994 | Blaha et al. |
| 5,499,309 A | 3/1996 | Kozuka et al. |
| 5,501,226 A * | 3/1996 | Petersen ............ A61B 3/1233 356/28.5 |
| 5,688,264 A | 11/1997 | Ren et al. |
| 5,835,189 A * | 11/1998 | Quigley ............ A61B 3/12 351/206 |
| 5,892,569 A * | 4/1999 | Van de Velde ...... A61F 9/008 351/221 |
| 5,921,981 A | 7/1999 | Bahmanyar et al. |
| 5,960,133 A | 9/1999 | Tomlinson |
| 5,993,441 A | 11/1999 | Muller et al. |
| 6,004,314 A | 12/1999 | Wei et al. |
| 6,066,128 A | 5/2000 | Bahmanyar et al. |
| 6,080,148 A | 6/2000 | Damasco et al. |
| 6,090,102 A | 7/2000 | Telfair et al. |
| 6,096,028 A | 8/2000 | Bahmanyar et al. |
| 6,099,522 A * | 8/2000 | Knopp et al. ............ 606/10 |
| 6,108,471 A | 8/2000 | Zhang et al. |
| 6,129,723 A | 10/2000 | Anderson et al. |
| 6,142,988 A | 11/2000 | Strahle et al. |
| 6,172,813 B1 | 1/2001 | Tadic-Galeb et al. |
| 6,193,710 B1 | 2/2001 | Lemberg |
| 6,473,236 B2 | 10/2002 | Tadic-Galeb et al. |
| 6,535,664 B1 | 3/2003 | Anderson |
| 6,595,985 B1 | 7/2003 | Tobinick |
| 6,648,876 B2 | 11/2003 | Murakami |
| 6,652,511 B1 | 11/2003 | Tomita |
| 6,671,428 B1 | 12/2003 | Yang et al. |
| 6,680,803 B2 | 1/2004 | Schultz et al. |
| 6,792,028 B2 | 9/2004 | Cook et al. |
| 6,792,178 B1 | 9/2004 | Zhou |
| 6,842,239 B2 | 1/2005 | Bastue et al. |
| 6,845,184 B1 | 1/2005 | Yoshimura et al. |
| 6,868,205 B2 | 3/2005 | Weverka et al. |
| 6,978,062 B2 | 12/2005 | Rose et al. |
| 7,146,983 B1 | 12/2006 | Hohla et al. |
| 7,261,687 B2 | 8/2007 | Yang |
| 7,364,543 B2 | 4/2008 | Yang et al. |
| 7,444,057 B2 | 10/2008 | Dacquay et al. |
| 7,499,624 B2 | 3/2009 | Dacquay et al. |
| 7,539,367 B2 | 5/2009 | Tamura et al. |
| 7,566,173 B2 | 6/2009 | Auld et al. |
| 7,648,242 B2 | 1/2010 | Ferguson et al. |
| 7,724,990 B2 | 5/2010 | Ishida |
| 7,980,745 B2 | 7/2011 | Shanbaky |
| 8,029,501 B2 | 10/2011 | Miller |
| 8,165,838 B2 | 4/2012 | Kane et al. |
| 8,277,048 B2 | 10/2012 | Artsyukhovich et al. |
| 8,292,434 B2 | 10/2012 | Horvath et al. |
| 8,325,988 B2 | 12/2012 | Ren et al. |
| 8,333,482 B2 | 12/2012 | Papac et al. |
| 8,398,240 B2 | 3/2013 | Smith |
| 8,449,147 B2 | 5/2013 | Papac et al. |
| 8,474,977 B2 | 7/2013 | Hahn et al. |
| 8,480,279 B2 | 7/2013 | Papac et al. |
| 8,485,972 B2 | 7/2013 | Papac et al. |
| 8,496,331 B2 | 7/2013 | Smith |
| 8,568,393 B2 | 10/2013 | Palanker |
| 8,571,364 B2 | 10/2013 | Smith et al. |
| 8,573,801 B2 | 11/2013 | Artsyukhovich et al. |
| 2001/0010003 A1 | 7/2001 | Lai |
| 2001/0046132 A1* | 11/2001 | Lanzetta ............ A61F 9/008 362/276 |
| 2001/0046351 A1 | 11/2001 | Kropp |
| 2002/0099363 A1 | 7/2002 | Woodward et al. |
| 2002/0125228 A1 | 9/2002 | Smart et al. |
| 2003/0231827 A1 | 12/2003 | Anderson et al. |
| 2004/0098070 A1 | 5/2004 | Mohr et al. |
| 2004/0111133 A1 | 6/2004 | Huculak et al. |
| 2005/0020926 A1 | 1/2005 | Wiklof et al. |
| 2005/0141068 A1 | 6/2005 | DeBenedictis et al. |
| 2006/0020309 A1 | 1/2006 | Altshuler et al. |
| 2006/0084954 A1 | 4/2006 | Zadoyan et al. |
| 2006/0111697 A1 | 5/2006 | Brinkmann et al. |
| 2006/0122584 A1 | 6/2006 | Bommannan et al. |
| 2006/0139722 A1 | 6/2006 | Kayser et al. |
| 2006/0187521 A1 | 8/2006 | Balle et al. |
| 2006/0217691 A1 | 9/2006 | Schuele et al. |
| 2006/0217695 A1 | 9/2006 | DeBenedictis et al. |
| 2007/0265602 A1 | 11/2007 | Mordaunt et al. |
| 2008/0015553 A1 | 1/2008 | Zaharias |
| 2008/0043353 A1 | 2/2008 | Horvath et al. |
| 2008/0080206 A1 | 4/2008 | Charles |
| 2008/0167642 A1 | 7/2008 | Palanker et al. |
| 2008/0269728 A1 | 10/2008 | Buczek et al. |
| 2009/0015923 A1 | 1/2009 | Auld et al. |
| 2009/0093800 A1 | 1/2009 | Auld et al. |
| 2009/0093798 A1 | 4/2009 | Charles |
| 2009/0163898 A1 | 6/2009 | Gertner et al. |
| 2009/0257065 A1 | 10/2009 | Hauger et al. |
| 2010/0137849 A1 | 6/2010 | Hanft et al. |
| 2010/0228119 A1 | 9/2010 | Brennan et al. |
| 2010/0228123 A1 | 9/2010 | Brennan et al. |
| 2010/0228124 A1 | 9/2010 | Brennan et al. |
| 2010/0228132 A1 | 9/2010 | Brennan et al. |
| 2010/0228238 A1 | 9/2010 | Brennan et al. |
| 2010/0249760 A1 | 9/2010 | Blumenkranz et al. |
| 2010/0318074 A1 | 12/2010 | Brennan et al. |
| 2011/0028951 A1 | 2/2011 | Raksi et al. |
| 2011/0090458 A1 | 4/2011 | Sakagawa |
| 2011/0116040 A1 | 5/2011 | Biernat et al. |
| 2011/0122366 A1 | 5/2011 | Smith |
| 2011/0141759 A1 | 6/2011 | Smith |
| 2011/0144627 A1 | 6/2011 | Smith |
| 2011/0144745 A1 | 6/2011 | Martin et al. |
| 2011/0160709 A1 | 6/2011 | McArdle et al. |
| 2011/0245815 A1 | 10/2011 | Abe |
| 2011/0279821 A1 | 11/2011 | Brennan et al. |
| 2011/0282190 A1 | 11/2011 | Caffey et al. |
| 2011/0282191 A1 | 11/2011 | Brennan et al. |
| 2011/0282331 A1 | 11/2011 | Brennan et al. |
| 2012/0075639 A1 | 3/2012 | Brennan et al. |
| 2012/0157828 A1 | 6/2012 | Huculak et al. |
| 2012/0190921 A1 | 7/2012 | Yadlowsky et al. |
| 2012/0191078 A1 | 7/2012 | Yadlowsky et al. |
| 2012/0203075 A1 | 8/2012 | Horvath et al. |
| 2012/0245569 A1 | 9/2012 | Papac et al. |
| 2012/0283523 A1 | 11/2012 | Yadlowsky et al. |
| 2013/0041233 A1 | 2/2013 | Yadlowsky et al. |
| 2013/0041356 A1 | 2/2013 | Smith et al. |
| 2013/0057821 A1 | 3/2013 | Auld et al. |
| 2013/0058533 A1 | 3/2013 | Ren et al. |
| 2013/0077917 A1 | 3/2013 | Lassalas et al. |
| 2013/0079598 A1 | 3/2013 | Auld et al. |
| 2013/0144278 A1 | 6/2013 | Papac et al. |
| 2013/0150839 A1 | 6/2013 | Smith et al. |
| 2013/0158392 A1 | 6/2013 | Papac et al. |
| 2013/0158393 A1 | 6/2013 | Papac et al. |
| 2013/0141672 A1 | 7/2013 | Smith |

FOREIGN PATENT DOCUMENTS

| | | |
|---|---|---|
| JP | 5299753 | 11/1993 |
| JP | 9313496 | 12/1997 |
| JP | 2003325541 | 11/2003 |
| JP | 2011-501985 | 1/2011 |
| JP | 2011-212349 | 10/2011 |
| TW | 200307530 | 12/2003 |
| WO | WO 0126591 | 4/2001 |
| WO | WO 01091458 | 11/2001 |
| WO | WO 0191661 | 12/2001 |
| WO | WO 02076119 | 9/2002 |
| WO | WO 02076319 | 10/2002 |

(56) References Cited

FOREIGN PATENT DOCUMENTS

| WO | WO 2005007002 | 1/2005 |
|---|---|---|
| WO | WO 2005089185 | 9/2005 |
| WO | WO 2006/091890 | 8/2006 |
| WO | WO 2009009246 | 1/2009 |
| WO | WO 2009/045286 | 4/2009 |
| WO | 2010/030159 | 3/2010 |
| WO | WO 2010/130456 | 11/2010 |
| WO | WO 2013085736 | 6/2013 |

OTHER PUBLICATIONS

Xu, ZhiWen, et al, "The Blood Vessel Recognition of Ocular Fundus," 7th Argentinian Symposium on Artificial Intelligence, Aug. 29-30, 2005, pp. 183-190, Rosario Argentina (8 pages).

Derakhshani, Reza, et al., "ATexture-Based Neural Network Classifier for Biometric Identification Using Ocular Surface Vasculature," Proceedings of International Joint Conference on Neural Networks, Aug. 2007, Orlando, USA (6 pages).

Helferty, J. P., et al, "System for Live Virtual Endoscopic Guidance of Bronchoscopy," Journal Computer Vision and Image Understanding, Oct. 2007, pp. 171-187, vol. 108, Issue 1-2 (8 pages).

Al-Hussainy, S. et al., "Pain Response and Follow-Up of Patients Undergoing Panretinal Laser Photocoagulation With Reduced Exposure Times" (online), (retrieved from www.nature.com/eye/journal/v22/n1/full/6703026a.pdf Nov. 23, 2007 (retrieved on Aug. 16, 2010) Nature Publishing Group (4 pages).

Sanghvi, C. et al., "Initial Experience with the Pascal Photocoagulator: A Pilot Study of 75 Procedures" (online), (retrieved from bjo.bmj.com/conent/92/8/1061.full.pdf) British Journal of Ophthalmology, Jun. 27, 2008 (retrieved on Aug. 16, 2010) (4 pages).

Extended European Search Report and Annex to the European Search Report issued for EP Application No. 12848530 dated Jul. 7, 2014, 6 pgs.

Pomerantzeff, Oleg et al., "A Method to Predetermine the Correct Photocoagulation Dosage", Laboratory Sciences, Archives of Ophthalmology, American Medical Association, US, vol. 101, No. 6, Jun. 1983, pp. 949-953.

International Search Report for PCT/US2012/51862, Publication No. WO2013/070300, 2 pages, dated Nov. 5, 2012.

Inderfurth, J.H.C. et al., "Dynamic reflectometer for control of laser photocoagulation on the retina", Lasers in Surgery and Medicine, vol. 15, 1994, pp. 54-61.

Jerath, M.R. et al., "Reflectance feedback control of photocoagulation in vivo", Archives of Ophthalmology, vol. 111, 1993, pp. 531-534.

English Translation of Japanese Office Action issued for Japanese Application No. 2014-539944, dated Aug. 24, 2015 (dated Sep. 1, 2015), 6 pgs.

Crihalmeanu et al. "Enhancement and Registration Schemes for Matching Conjunctival Vasculature," ICB 2009, LNCS 5558, pp. 1240-1249, 2009.

Frieberg, M.D., et al., The Treatment of Macular Disease Using a Micropulsed and Continuous Wave 810-nm Diode Laser, Ophthalmology, Dec. 1997, vol. 104, No. 12.

Han, et al. "Handheld Forward-Imaging Needle Endoscope for Ophthalmic Optical Coherence Tomography Inspection," Journal of Biomedical Optics 13(2), Mar./Apr. 2008, pp. 020505-1 to 020505-3.

Jelinkova, et al., "Hollow Waveguide Delivery Systems for Laser Technological Application," Progress in Quantum Electronics, Nov. 1, 2003, pp. 145-164, vol. 28, Issues 3-4, Elsevier, Ltd.

Muqit, M. M., Denniss, J., Nourrit, V., Marcellino, G. R., Henson, D. B., Schiessl, I., & Stanga, P. E., Spatial and Spectral Imaging of Retinal Laser Photocoagulation Burns, Investigative Ophthalmology & Visual Science, Feb. 2011, vol. 52(2), pp. 994-1002.

Regillo et al., "Vitreoretinal Disease: The Essentials," 1998.

Solouma et al., "A New Real-Time Retinal Tracking System for Image-Guided Laser Treatment," IEEE Transactions on Biomedical Engineering, Sep. 2002; vol. 49, No. 9, pp. 1059-1067.

Wu, et al. "Paired-Angle-Rotation Scanning Optical Coherence Tomography Forward-Imaging Probe," Optics Letters, vol. 31, No. 9, May 1, 2006, pp. 1265-1267.

Xu et al., Abstract—"The Blood Vessel Recognition of Ocular Fundus," Proceeding of 2005 International Conference, Machine Learning and Cybernetics, Aug. 18-21, 2005, vol. 7, pp. 4493-4498.

Yamada, Y., Suzuma, K., Fujikawa, A., Kumagami, T., & Kitaoka, T., Imaging of Laser-Photocoagulated Diabetic Microaneurysm with Spectral Domain Optical Coherence Tomography, Retina, Apr. 2013, vol. 33(4), pp. 726-731.

Yaqoob et al., "Methods and Application Areas of Endoscopic Optical Coherence Tomography," Journal of Biomedical Optics, 11(6), Nov./Dec. 2006, pp. 063001-1 to 063001-19.

International Search Report, PCT/US2006/038086; dated Feb. 14, 2007, 3 pages.

Written Opinion, PCT/US2006/038086, dated Feb. 14, 2007, 6 pages.

Partial European Search Report for Application No. 07111216.3, Publication No. 1872754,dated Oct. 10, 2007, 3 pages.

Search Report from Taiwan, Patent Application No. 0701003258, Publication No. 93979/258, Published Feb. 27, 2009, 1 page.

Extended European Search Report and Annex to the European Search Report issued for EP Application No. 12855412 dated Mar. 24, 2015, 4 pgs.

International Search Report, PCT/US2012/066538, Feb. 8, 2013, 3 pages.

Written Opinion of the International Searching Authority, PCT/US2012/066538, Feb. 8, 2013, 5 pages.

PCT International Preliminary Report on Patentability, PCT/US2012/051862, dated May 13, 2014, 8 pages.

English Translation of Chinese Office Action issued for Chinese Application No. 201280037670.X, dated Jun. 20, 2016, 13 pgs.

* cited by examiner

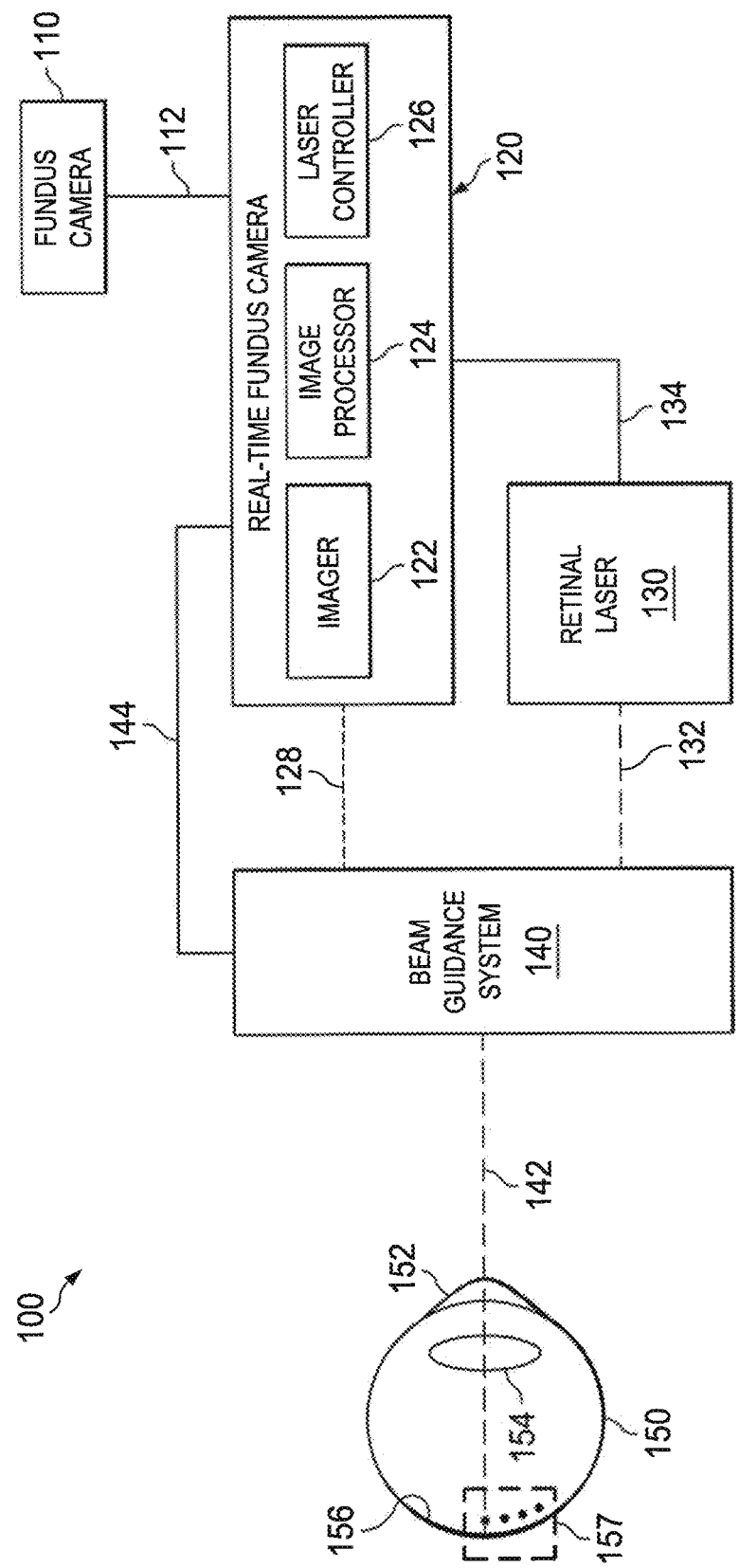

RETINAL LASER SURGERY

BACKGROUND

The present disclosure relates to optical surgery, id more specifically to surgery on a patient's retina via a laser.

Various diseases may be treated by applying a laser to a patient's retina For example, diabetic retinopathy may be therapeutically treated by creating multi-spot laser coagulation patterns on a patient's retina—panretinal photocoagulation, which may revitalize the retina. Often, these patterns require many (e.g., 3000) precision laser shots.

To apply retinal laser shots, a physician may, for example, individually target each shot and activate the laser. The shots may be applied directly to the retina (e.g., using an endo probe) or through the eye (e.g., using laser indirect ophthalmoscopy or a slit lamp with laser delivery optics). During a laser shot, a physician may adjust the shot (e.g., power and/or pulse length) to achieve a certain degree of retina whitening, which is correlated with a therapeutic effect. To decrease surgical time, tools have been developed that allow a physician to apply a number of shots at one time (e.g., multi-spot fibers and Pascal patterning laser).

BRIEF SUMMARY

In one general implementation, a process for retinal laser surgery may include identifying retina blood vessels from a retina image. The process may also include determining a retina location needing therapy and not substantially intersecting a retina blood vessel and generating a command to activate a retinal laser when a beam from the retinal laser is aligned with the therapeutic spot. The process may be performed using a number of system and computer program product configurations.

In some implementations, an image of the retina may be obtained and used to identify the retina blood vessels. In some instances, a real-time image of a retina may be obtained, retina blood vessels may be obtained from another retina image, and the retina blood vessels may be registered with the real-time retina image.

Particular implementations may include obtaining a real-time image of the retina. The real-time image of the retina may be used to identify the retina blood vessels. In other instances, the retina blood vessels may be registered with the real-time image of the retina. Furthermore, some implementations may include obtaining an additional retina image after one or more laser shots and registering the retina blood vessels with the third image.

Certain implementations may include adjusting a laser shot based on retinal characteristics. For example, the reflectivity of a retina spot needing therapy may be determined before application of a laser shot, and the laser shot may be adjusted based on the determined reflectivity. As another example, the reflectivity of a retina spot needing therapy may be determined during a laser shot, and the laser shot may be adjusted based on the determined reflectivity Some implementations may include adjusting the alignment of a laser beam. Particular implementations may include generating a laser shot for the therapeutic location.

Various implementations may include one or more features. For example, a therapeutic laser shot may be applied to a retina in an automated manner while avoiding blood vessels. Thus, automated retinal therapy may be achieved while avoiding damage to blood vessels. As another example, multiple laser shots may be applied in an automated manner while avoiding blood vessels. Thus, automated retinal therapy may be achieved over a relatively large area, which may reduce surgical time and effort, while avoiding blood vessel damage. Furthermore, since each therapeutic laser shot is individual, the shots may be accurately targeted.

The details and features of various implementations will be conveyed by the following description, along with the drawings.

BRIEF DESCRIPTION OF THE SEVERAL VIEWS OF THE DRAWINGS

FIG. 1 is a block diagram illustrating an example system for retinal laser surgery.

DETAILED DESCRIPTION

Figure 2A:
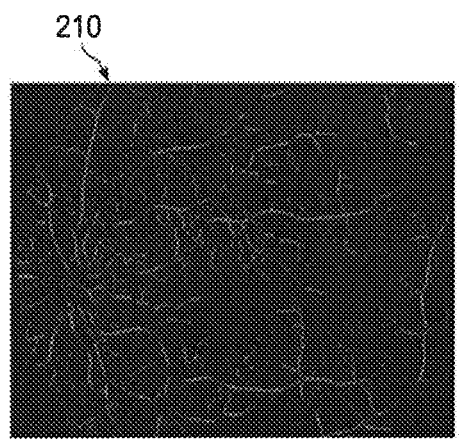
FIGS. 2A-B are drawings illustrating an example processing technique used by the retinal laser surgery system of FIG. 1.

FIG. 1 illustrates an example system 100 for retinal laser surgery. System 100 includes a fundus camera 110, a real-time fundus camera 120, a retinal laser 130, and a beam guidance system 140. System 100 is adapted to perform laser surgery on an eye 150, which includes a cornea 152, a lens 154, and a retina 156, by directing a laser beam at various points 157 on retina 156.

Fundus camera 110 is adapted to obtain a relatively high resolution image of retina 156 of eye 150. Fundus camera 110 may use, for example, fluorescein angiography to obtain the image. Fundus camera 110 may also obtain images of other parts of the fundus (e.g., optic disc, macula, and fovea). In certain implementations, fundus camera 110 may be a scanning laser ophthalmoscope ("SLO"). Fundus camera 110, though, may be any camera, still camera or video camera, that is operable to deliver an image of sufficient resolution to identify the retinal blood vessels. For example, the fundus camera 110 may be any camera that is operable to deliver high resolution or very high resolution images of retina blood vessels. Thus, fundus camera 110 may obtain pre-treatment or real-time images of retina 150.

Real-time fundus camera 120 is adapted to obtain real-time images of retina 156, associate a blood vessel pattern with the image, and control firing of retinal laser 130. To obtain real-time images, real-time fundus camera 120 includes an imager 122. Imager 122 may be, for example, an SLO, a video camera, or any other appropriate device for imaging a retina in real-time. A video camera may be used, for example, with a beamsplitter and a slit lamp with laser delivery optics. Note that a real-time image may or may not be one that is identical with current eye conditions. There may be, for example, a delay due to processing time. Moreover, a generated image may be used for a short period of time (e.g., a few seconds) and still be considered real-time. Real-time fundus camera 120 may also obtain images of other parts of the fundus (e.g., optic disc, macula, and fovea).

Real-time fundus camera 120 also includes an imager processor 124 and a laser controller 126. Image processor 124 is adapted to determine a blood vessel pattern based on the retina image from fundus camera 110 and associate the blood vessel pattern with the real-time image. Laser controller 126 is adapted to control firing of retinal laser 130. Imager 122, image processor 124, and laser controller 126 may each have their own processor or share a processor in other implementations, one or more of the imager 122, image processor 124, and laser controller 126 may share a processor. Moreover, they could be combined in the same unit.

in some implementations, fundus camera 110 and the real-time fundus camera 120 may obtain images with differing resolutions. That is, in some implementations, one of the cameras may obtain an image of the retina with a higher resolution than the other camera. Further, the cameras may utilize different imaging technologies to obtain images of the retina. In still other implementations, the cameras may obtain images having the same resolution or obtain images using the same or similar imaging technology.

In some instances, a single camera may be used to control a laser based on images produced by the camera. For example, in some instances, the fundus camera 110 may be eliminated. Thus, according to some implementations, an image produced by the real-time fundus camera 120 may be utilized to determine a retinal blood vessel pattern. In some instances, the real-time fundus camera 120 may be a high definition video camera in other instances, the real-time fundus camera 120 may be an SLO. However, any imaging device operable to produce a high resolution picture of the fundus showing retina blood vessels may be used. This retinal blood vessel pattern may be used to identify suitable locations for laser treatment. For example, the suitable locations for laser treatments may be locations of the retina that does not intersect a blood vessel. Accordingly, an image from the real-time fundus camera 120 may be processed by the image processor 124 to determine a blood vessel pattern.

Retinal laser 130 may generally be any laser for applying therapeutic laser shots to a retina. Retinal laser 130 may be, for example, a photocoagulation laser. For therapy, a retinal laser may have a power on the order of a few watts and a pulse length of up to a few hundred milliseconds. The power and/or pulse length of retinal laser 130 are typically controllable.

Beam guidance system 140 is adapted to guide light (visible or non-visible) from real-time fundus camera 120 and retinal laser 130 through cornea 152 and lens 154 to specific locations on retina 156 as a beam 142. Beam guidance system 140 may also guide light from retina 156 to real-time fundus camera 120. Beam guidance system 140 may include, for example, one or more mirrors driven by one or more servo drives or a rotating glass prism.

In some implementations, fundus camera 110 images retina 156 and passes the image data to real-time-fundus camera 120. Fundus camera 110 may pass the data to real-time fundus camera 120 using a communication link 112 (e.g., a bus or a local area network).

Image processor 124 of real-time fundus camera 120 may process an image of the retina to identify retinal blood vessels. As indicated above, in some implementations, the image of the retina may be obtained using the fundus camera 110. In other instances, the image of the retina may be obtained by the real-time fundus camera 120. The identification process may be accomplished by a variety of well know techniques. For example, in some instances, identification of retinal blood vessels may be accomplished according to the technique described in "The Blood Vessel Recognition of Ocular Fundus," *Proceedings of* 2005 *International Conference on Machine Learning and Cybernetics,* 2005, Aug. 18-21, 2005 by Zhi-Wen Xu et al. In other instances, retinal blood vessels may be identified using the technique described in "A Texture-Based Neural Network classifier for Biometric Identification using Ocular Surface Vasculature," *Proceedings of International Joint Conference on Neural Networks, August* 2007, by Reza Derakhshani et al. However, the scope of the disclosure is not so limited. Accordingly, any suitable technique for identifying retinal blood vessels may be used.

Before, during, or after this, imager 122 of real-time fundus camera 120 may image retina 156. For example, imager 122 may generate a light beam 128, and beam guidance system 140 may scan the light beam across retina 156 as beam 142.

In instances in which the blood vessels are identified from an image of the retina 156 obtained by the fundus camera 110, image processor 124 may register the blood vessel pattern with the real-time image obtained by the real-time fundus camera 120. That is, the blood vessel pattern obtained from an image from the fundus camera 110 may be aligned (e.g., scaled and accurately located) onto the image of the retina obtained by the real-time fundus camera 120. Registration may be accomplished, for example, by identifying specific features (e.g., optical disk, blood vessel branches, etc.). The two images may then be rotated and scaled to achieve an appropriate degree (e.g., maximum) of overlapping features. In implementations in which a single camera is used, registration may be eliminated.

Figure 2B:
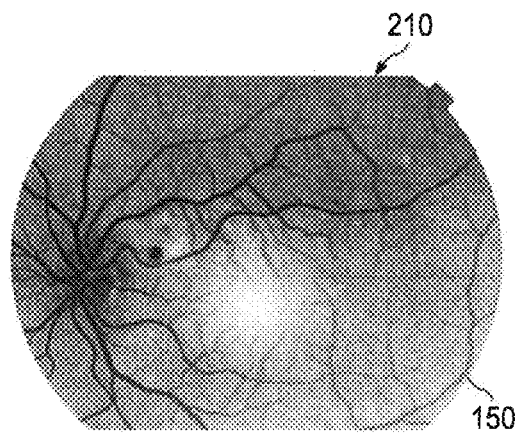

FIGS. 2A-B illustrate example images that may be generated by real-time fundus camera 120. In FIG. 2A, the real-time fundus camera has processed image data from fundus camera 110 to determine a retina blood vessel pattern 210. In FIG. 2B, real-time fundus camera 120 has registered blood vessel pattern 210 with a real-time image of eye 150.

Laser controller 126 of real-time fundus camera 120 may identify one or more locations for laser therapy on retina 156 within one or more defined regions of the retina 156. For example, a user, such as, for example, a physician or other medical professional, may identify a region of the retina 156 requiring treatment. In some instances, the user may identify a region of the retina 156 requiring treatment via interacting with a displayed image of the retina. For example, an image of the retina may be displayed on a display. In some instances, the display may be connected with or form part of a surgical console or computer system, such as the computer system shown in FIG. 8 discussed below. The user may interact with the image of the retina to select the region of the retina for treatment using an input device. For example, input devices such as a mouse, pen, trackball, or other device may be used to select a region of the retina for treatment. In other instances, the display may be a touch screen. Accordingly, the user may select the portion of the retina by touching the touch screen display, for example, with a finger or other instrument.

In addition to selecting a region of the retina for treatment, a user may also define other treatment settings. For example, a user may define one or more of laser power, laser on-time duration (i.e., the duration of time in which the laser is incident upon a retina location), spot size, and the spacing ("spot packing density") of spots to be formed on the retina.

Laser controller 126 may determine one or more therapeutic locations for laser treatment within the identified region(s). Laser controller 126 may determine the location(s) of one or more spots to be formed on the retina within the selected region, for example, by taking into account a variety of factors (e.g., spot size, spot packing density, etc.). Which may be set by the user. For example, a spot size may be 1 mm, and there may be 1 mm between spots.

Laser controller 126 determines whether a therapeutic location at which a spot is to be formed intersects with a retina blood vessel. For example, this determination may be based on the location's proximity to the blood vessel as well as the size of the spot to be created. If the therapeutic location intersects with a retina blood vessel, laser controller 126 may identify another location in need of therapy. In particular implementations, a small amount of intersection of a laser shot with a blood vessel (e.g., covering less than 10% of the blood vessel) may be allowable. Typically, laser power drops off away from the center of the beam.

Once laser controller 126 identifies a location in need of therapy and not intersecting a blood vessel, laser controller 126 may instruct beam guidance system 140 to align beam 142 with the therapeutic location. The instruction(s) may be sent, for example, across a data link 144 (e.g., a bus or local area network). Laser controller 126 may also instruct retinal laser 130 to fire when the beam guidance system has aligned a beam 132 with the therapeutic location. The instructions may be sent, for example, across a data link 134 (e.g., a bus or local area network). After retinal laser 130 has fired, laser controller 126 may determine another appropriate therapeutic location. For example, the laser controller 126 may determine another therapeutic location that does not intersect a blood vessel within the region for laser therapy. The laser controller 126 may also adjust beam guidance system 140 to align with the new therapeutic location and instruct retinal laser 130 to fire again.

Figure 3:
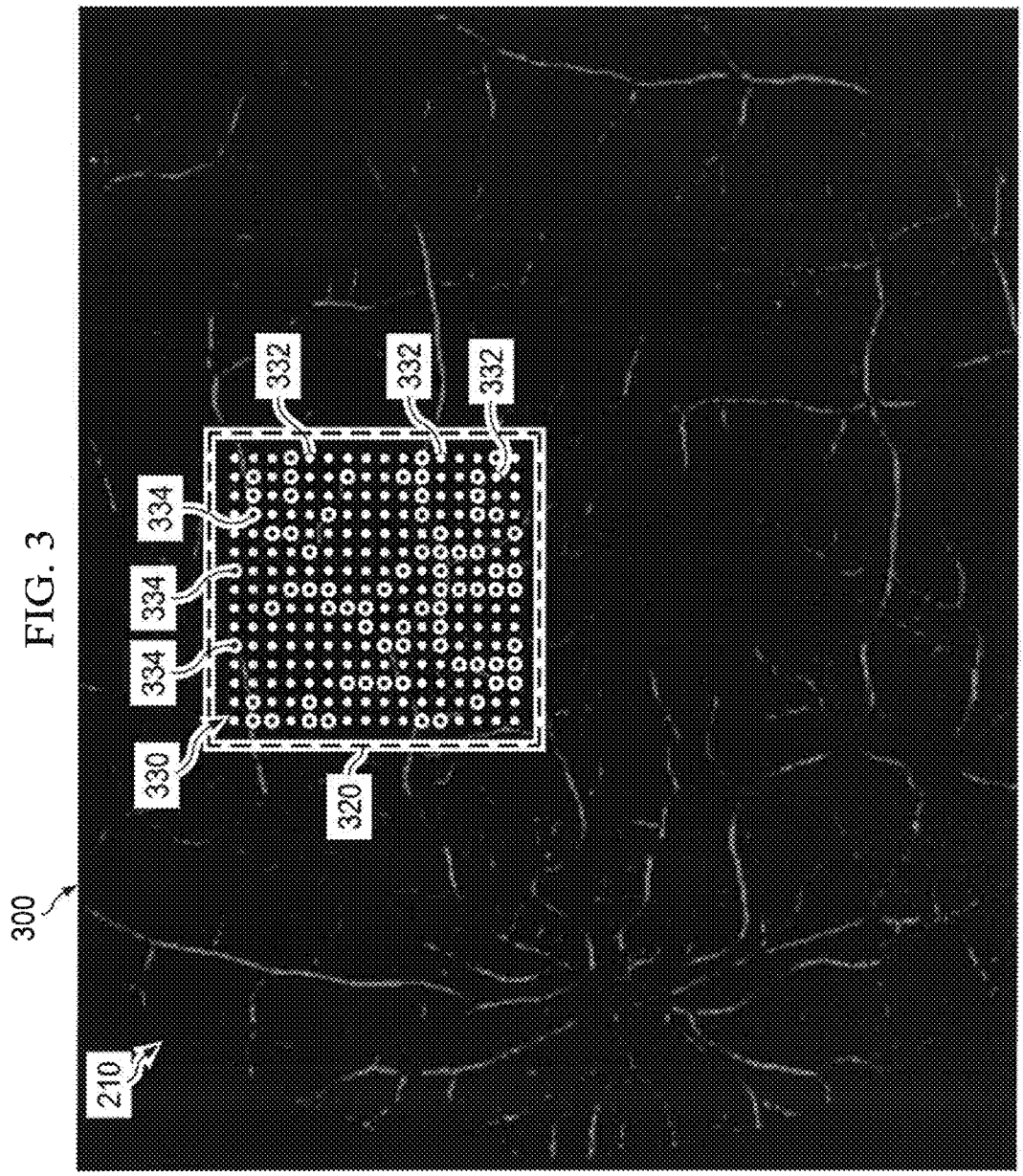
FIG. 3 is a drawing illustrating an example therapeutic technique applied by the retinal laser surgery system of FIG. 1.

FIG. 3 illustrates a therapeutic technique that may be achieved using system 100 to perform retinal laser surgery. In general, FIG. 3 illustrates a retina image 300 with a blood vessel pattern 210 superimposed thereupon. In image 300, a region 320 has been defined for retinal laser surgery by a user, such as, for example, a physician or other medical professional. Region 320 has a number of locations 330 that have been identified for potential application of a laser beam. In some instances, the locations 330 may be determined, for example, based on the user's setting of spot size and spacing. In some instances, locations 330 may be determined manually. In other instances, locations 330 may be determined by a processor. Locations 330 include locations 332 and locations 334. Locations 332 do not intersect blood vessels 330, and locations 334 do intersect blood vessels 330. Thus, locations 332 are to be treated by a retinal laser while locations 334 are not to be treated.

System 100 may also include other operations. For example, real-time fundus camera 120 may image eye 150 periodically. The eye 150 may be imaged periodically to redetermine the eye's position. For example, in some implementations, the real-time fundus camera 120 may repeatedly image the retina 156 at a defined frequency, such as a defined period of time, between laser shots, etc. The real-time fundus camera may then make adjustments to its targeting of retinal laser 130 if the eye has moved. In some instances, approximately 5 ms may elapse between eye movements due to saccadic movement. The periodic images may be taken at one or more times between eye movements to accurately target the retinal laser 130. A windowing CMOS camera having a high partial frame rate, for example, may be used to provide the rapid (i.e., high frame rate) image capture.

As another example, image processor 124 may determine the reflectivity of a therapeutic location on a retina before retinal laser 130 is activated and adjust the laser shot based on this determination. In particular implementations, for instance, a retina location may need to be heated to around 50 degrees C. to achieve a therapeutic effect. However, the heating depends on its reflectivity, as well as treatment laser spot diameter and wavelength.

The reflectivity of a location of the retina may be determined, for example, based on the intensity of light reflected to fundus camera 110 or real-time fundus camera 120, the greater the amount of light reflected indicating higher reflectivity. The proper characteristics for a laser shot to have an enhanced therapeutic effect are dependent on the color of the retina, which may vary from location to location within eye 150, and reflectivity may be correlated with color. For example, 30% reflectivity may correlate with a brown color, and 80% reflectivity may correlate with an orange color. A location having higher reflectivity may call for a more intense laser shot (e.g., increased power and/or pulse length), and a location having lower reflectivity may call for a less intense laser shot. By evaluating a therapeutic location before the retinal laser is activated and adjusting the laser shot (e.g., power and/or pulse length), real-time fundus camera 120 may provide an enhanced therapeutic effect at a location. Moreover, the adjustments may be made on a location by location basis.

As a further example, real-time fundus camera 120 may determine reflectivity of retina 156 at a therapeutic location during a laser shot and command retinal laser 130 to adjust the laser shot (e.g., power and/or pulse length) based on the determined reflectivity. The therapeutic effect provided to a retina location may be determined by the degree of whitening that occurs due to a laser shot, and whitening can be correlated with reflectivity. Thus, by evaluating a therapeutic location while the retinal laser is operating and adjusting the laser shot, real-time fundus camera 120 may provide an enhanced therapeutic effect. In particular implementations, the laser shot may be terminated as soon as a preset value of retina whitening has been achieved for the retina location.

System 100 has a variety of features. For example, system 100 applies a therapeutic laser shot to a retina While avoiding blood vessels. Thus, automated retinal therapy may be achieved while avoiding damage to blood vessels. Additionally, multiple laser shots may be applied in an automated manner while avoiding blood vessels. Thus, automated retinal therapy may be achieved over a relatively large area, which may reduce surgical time and effort, while avoiding blood vessel damage. Furthermore, since each therapeutic laser shot is individual, it may be accurately targeted. System 100 may be useful for generating a variety of therapeutic effects, including treating diabetic retinopathy, activating photo dynamic therapy, and treating macular degeneration.

Although FIG. 1 illustrates one implementation of a system for retinal laser surgery, other systems for retinal laser surgery may have fewer, additional, and/or a different arrangement of components. For example, the image processor and the laser controller may be part of the same subsystem. For instance, they may be part of the same computer. As another example, the image processor and the laser controller may not be part of the real-time fundus camera. For instance, they may be separate subsystems coupled together by one or more communication networks.

Additionally, system 100 may include additional components (e.g., a beam combiner). As another example, system 100 may not include fundus camera 110. For instance, real-time fundus camera 120 may provide the retina image from which the blood vessel pattern is determined. For example, a real-time fundus camera having a resolution sufficient to detect the blood vessel pattern may be used. Thus, a single camera may be used to control a laser based on images produced by the camera. In these implementations, the blood vessel pattern may not have to be registered with the real-time image. Other systems may also apply therapeutic techniques similar to those illustrated in FIG. 3.

Figure 4:
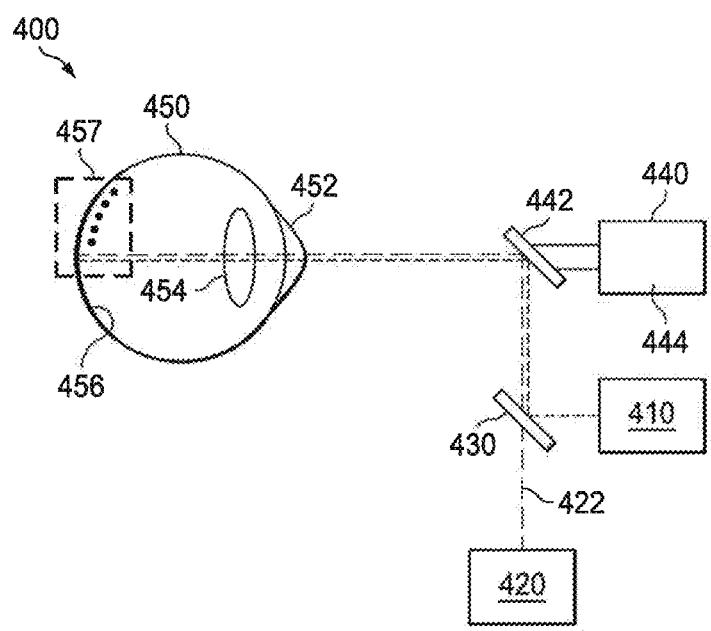
FIG. 4 is a schematic diagram illustrating another example system for retinal laser surgery.

FIG. 4 illustrates another example system 400 for retinal laser surgery. System 400 includes a real-time fundus camera 410, a retinal laser 420, a beam combiner 430, and a beam guidance system 440. System 400 is adapted to perform laser surgery on an eye 450, which in includes a cornea 452, a lens 454, and a retina 456.

In this implementation, real-time fundus camera 410 may include, for example, an SW, and retinal laser 420 may be, for example, a photocoagulation laser. Beam combiner 430 is adapted to combine the beams from real-time fundus camera 410 and retinal laser 420.

Beam combiner 430 may be, for example, a beam splitter that combines light of different wavelengths (whether visible or non-visible). For instance, treatment lasers are often green (e.g., 514 nm) or yellow (e.g., 577 nm), and the imaging laser may be in the near IR, which may reduce patient discomfort. Moreover, using a different wavelength for the imaging laser may produce better image quality. Thus, real-time fundus camera 410 may operate in one spectral band (e.g., 800 nm), and retinal laser 420 may operate in another spectral band (e.g., 532 nm).

Beam guidance system 440 is adapted for directing beams from real-time fundus camera 410 and retinal laser 420 to various locations 457 on the retina 456. In this implementation, beam guidance system 440 includes a galvanometer mirror 442 and a galvanometer drive 444. In response to input commands, galvanometer drive 444 adjusts the orientation of galvanometer mirror 442, which adjusts the direction of the beams. In particular implementations, beam guidance system 440 may include multiple mirrors and drives.

in certain modes of operation, real-time fundus camera 410 may process one or more images of retina 456 to identify retina blood vessels. For example, the images may come from a fundus camera (not shown) that passes the image data to real-time fundus camera 410, or fundus camera 410 may itself image retina 456. Real-time fundus camera 410 may also obtain a real-time image of retina 456 and register the blood vessel pattern with the image.

Real-time fundus camera 410 may also identify one or more locations 457 in need of therapy on retina 456. For example, real-time fundus camera 410 may identify a location by identifying a predetermined location in need of therapy or determining a location based on an indication (e.g., user input) regarding a region in need of therapy. Real-time fundus camera 410 also determines whether the therapeutic location intersects with a blood vessel. In some instances, intersection may be determined based on the location's proximity to a blood vessel as well as a size (e.g., diameter) of a spot to be formed at the location. If the therapeutic location intersects with a blood vessel, real-time fundus camera 410 may identify another location in need of therapy.

Once real-time fundus camera. 410 identifies a location in need of therapy and not intersecting a blood vessel, real time fundus camera 410 may instruct beam guidance system 440 to align a beam 422 from retinal laser 420 with the location. Real-time fundus camera 410 may also instruct retinal laser 420 to fire when the beam guidance system has aligned beam 422 with the therapeutic location. After retinal laser 420 has fired, real-time fundus camera 410 may determine another appropriate therapeutic location, adjust beam guidance system 440, and instruct retinal laser 420 to fire again.

System 100 may also include other operations. For example, real-time fundus camera 410 may image eye 450 periodically (e.g., every few seconds or between each laser shot) to redetermine the eye's position. The real-time fundus camera may then make adjustments to its targeting of retinal laser 420 if the eye has moved. Typically, it takes the eye about 5 ms to move. Thus, there is time for making adjustments.

As another example, real-time fundus camera 410 may determine the reflectivity of a therapeutic location on a retina before retinal laser 420 is activated and adjust the laser shot based on this determination. For example, the reflectivity of a location may be determined based on the light reflected to real-time fundus camera 410, the greater the amount of light reflected indicating higher reflectivity. The proper characteristics for a laser shot to have an enhanced therapeutic effect may be dependent on the color of the retina, which may vary from location to location within eye 150, and reflectivity may be correlated with color. A location having higher reflectivity may call for a more intense laser shot (e.g., increased power and/or pulse length), and a location having lower reflectivity may call for a less intense laser shot. By evaluating a therapeutic location before the retinal laser is activated and adjusting the laser shot (e.g., power and/or pulse length), real-time fundus camera 410 may provide an enhanced therapeutic effect at a location. Moreover, the adjustments may be made on a location by location basis.

As a further example, real-time fundus camera 410 may determine the reflectivity of retina 456 at a therapeutic location during a laser shot and command retinal laser 420 to adjust the laser shot (e.g., power or pulse length) based on the determined reflectivity. Real-time fundus camera 410 may determine the reflectivity of a therapeutic location during a laser shot by sampling the retina in the same or a different spectral band than that used by retinal laser 420. When whitening of the retina occurs, reflectivity changes in a wide range of wavelengths. Beam combiner 430 may combine the beam from real-time fundus camera 410 with that from retinal laser 420, and beam guidance system 440 may guide the combined beams to the therapeutic location. The reflected part of the beam from real-time fundus camera 410 may then be sent from beam guidance system 440 to beam combiner 430, which may direct it back to real-time fundus camera 410 for detection and analysis.

Figure 5:
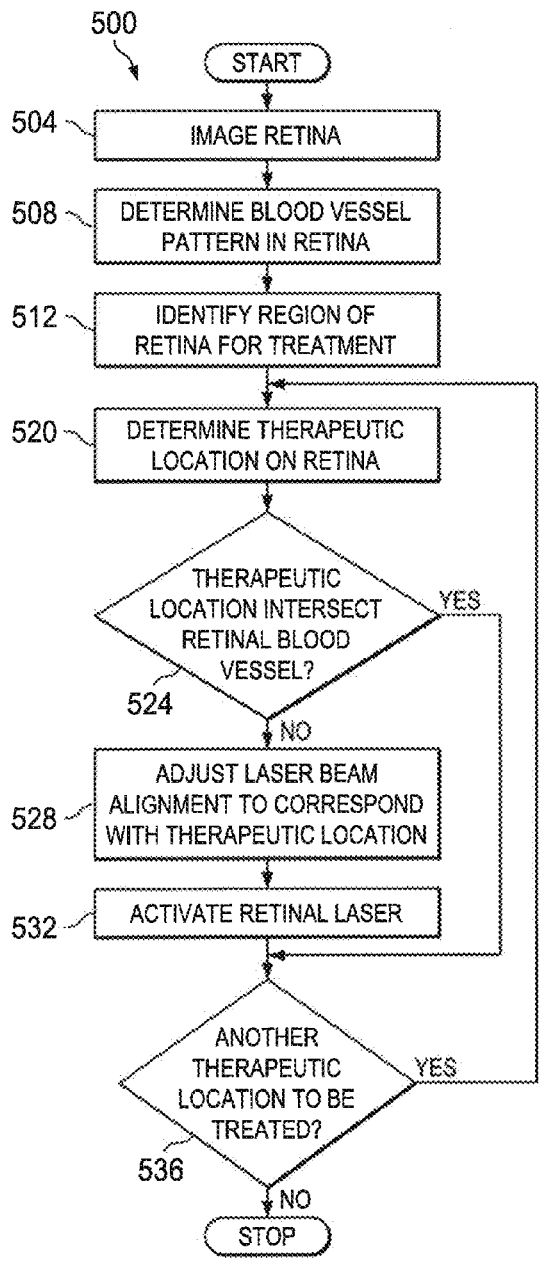
FIG. 5 is a flowchart illustrating an example process for retinal laser surgery.

FIG. 5 illustrates an example process 500 for retinal surgery. In some instances, process 500 may be accomplished by a system similar to system 100 or system 400.

Process 500 calls for imaging a retina (operation 504). In some implementations, a retina may be imaged using a real-time fundus camera, an SLO, or other appropriate device. In some instances, fluorescein angiography may be used to obtain images of the retina. In other instances, a live image of the retina may be obtained. In some implementations, any high definition video camera may be used to produce a live image. For example, in some instances, a high definition video camera coupled to a slit lamp may be used.

At 508, a blood vessel pattern of the retina may be determined based on the obtained retinal image. The blood vessel pattern may be determined using one or more well-known algorithms or any other suitable technique. For example, one of the techniques disclosed above may be used. However, the disclosure is not so limited. Thus, any suitable technique may be used.

In some instances, a second image of the retina may be obtained. For example, the second image may be obtained from a second camera. The second camera may be a real-time fundus camera. In some implementations, the first fundus camera and the second fundus camera may obtain images with differing resolutions. That is, in some implementations, one of the cameras may obtain an image of the retina with a higher resolution than the other camera. Further, the first and second cameras may utilize different imaging technologies to obtain images of the retina. In still other implementations, the first and second camera may obtain images having the same resolution or obtain images using the same or similar imaging technology.

For example, in implementations using a second camera, the second camera may obtain a real-time image of the retina. In some instances, the second camera may be an SLO or video camera. The blood vessel pattern may be registered with the real-time image of the retina.

At 512, a therapeutic region of the retina may be identified for treatment. For example, identifying the therapeutic region of the retina may be accomplished by receiving input from a user, such as, for example, a physician or other medical professional. In some instances, input from the user may be accomplished by user interaction with a displayed image of the retina to define the region of the retina for treatment. For example, input may be received through an input device, such as, for example, a touch screen, mouse, keyboard, track ball, or other input device.

At 520, one or more locations may be determined within the identified therapeutic region of the retina. In some instances, a user may identify a location within the identified region as a starting point of the locations for therapy. In other instances, one or more of the therapeutic locations may be identified by retrieving previously identified therapeutic locations. The therapeutic locations in a region may be arranged according to a variety of factors. For example, the therapeutic locations may be arranged according to the size of the therapeutic laser spots to be formed and their packing density. These factors may be input by the user.

Process 500 also calls for determining Whether the therapeutic location intersects with a retinal blood vessel (operation 524). In some instances, a therapeutic location may be considered to intersect a retinal blood vessel if the location overlays any portion of the retinal blood vessel. Further, a therapeutic location may be determined to intersect a blood vessel if the location overlays a blood vessel or if the therapeutic spot to be formed at the location would intersect a retinal blood vessel. A spot may be determined to intersect a blood vessel based upon the size (e.g., diameter) of the spot to be formed. For example, a spot may be determined to intersect a blood vessel if the spot overlays the blood vessel by a selected amount. In some implementations, a small amount of intersection is allowable.

If the therapeutic location does not intersect with a retinal blood vessel, process 500 calls for adjusting the alignment of a laser beam to correspond with the therapeutic location (operation 528). The alignment of a laser beam may be adjusted, for example, by a galvanometer mirror/drive system. Process 500 also calls for activating a retinal laser (operation 532). The laser may be activated, for example, at a predefined power and pulse length.

Process 500 also calls for determining whether there is another retinal therapeutic location to be treated (operation 536). Often, the retinal region requiring therapeutic treatment is relatively large compared to the spot formed by the laser, and thus, there may be many (e.g., thousands) therapeutic locations in need of treatment.

If there is another therapeutic location to be treated, process 500 calls for determining another therapeutic location (operation 520). If, however, there is not another therapeutic location to be treated, process 500 is at an end.

Returning to operation 524, if a therapeutic location does intersect a blood vessel, process 500 calls for determining whether another therapeutic location is to be treated (operation 536). That is, process 500 skips the therapeutic treatment for a location that intersects a blood vessel. If there is another therapeutic location to be treated, process 500 calls for determining another therapeutic location (operation 520), and if there is not another therapeutic location to be treated, process 500 is at an end.

Although process 500 illustrates an example process for retinal laser surgery, other processes for retinal laser surgery may include fewer, additional, and or a different arrangement of operations. For example, a process may not include imaging a retina. In some instances, this may occur if the retina has been imaged at another point. As another example, a process may include obtaining a real-time image of the retina. The real-time image may be obtained, for example, using an SLO, a video camera, or other suitable device. The blood vessel pattern may be registered with the real-time image. In some instances, the real-time image of the retina and one or more other image(s) of the retina may have differing resolutions. Further, the real-time image of the retina and one or more other image(s) of the retina may be obtained using different cameras. Alternatively, the images of the retina may be obtained by the same camera at differing resolutions. In still other instances, the retina images may be obtained by the same camera at the same resolution. The therapeutic region may be identified using the real-time image with the retina blood vessels registered thereon.

As an additional example, a process may include evaluating a number (e.g., two or more) of therapeutic locations for intersection with a blood vessel before adjusting the laser. Thus, a process may determine beforehand which therapeutic locations are viable. As a further example, a process may include scanning the eye (e.g., with an SLO) to make sure it is in the same position before performing another therapeutic laser shot. As a further example, a process may include adjusting a laser shot before or during the laser shot, which will be discussed below. Adjustments to laser shots may be made based on variability limits established by a user.

Figure 6:
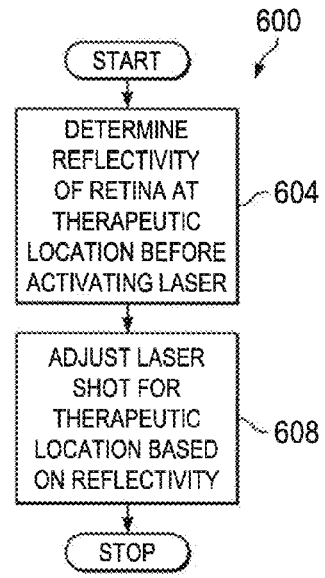
FIG. 6 is a flowchart illustrating another example process for retinal laser surgery.

FIG. 6 illustrates another example process 600 for retinal laser surgery. In some implementations, process 600 may be accomplished by a system similar to system 100 or system 400. However, these systems are provided merely as examples. Thus, other systems may also be used to accomplish process 600. Process 600 may also be used as part of another process for retinal surgery, process 500, for example. Process 600 may be repeated several times during a surgical procedure.

Process 600 calls for determining reflectivity of a therapeutic location on a retina before activating a laser (operation 604). In some instances, the reflectivity may be determined based on the light reflected to an SLO, the greater the amount of light reflected indicating higher reflectivity.

Process 600 also calls for adjusting a laser shot for the therapeutic location based on the reflectivity (operation 608). For example, a location having higher reflectivity may call for a more intense laser shot (e.g., increased power and/or pulse length.), and a location having lower reflectivity a call for a less intense laser shot. Process 600 is then at an end.

Figure 7:
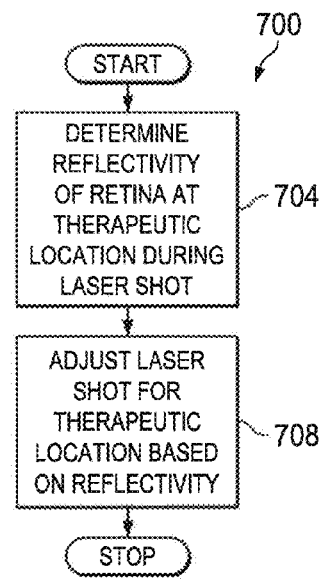
FIG. 7 is a flowchart illustrating an additional example process for retinal laser surgery.

FIG. 7 illustrates an additional example process 700 for retinal laser surgery. In some instances, process 700 may be accomplished by a system similar to system 100 or system 400. However, these systems are provided merely as examples. Thus, other systems may also be used to accomplish process 700. Process 700 may also be used as part of another process for retinal surgery, process 500, for example. Process 700 may be repeated several times during a surgical procedure.

Process 700 calls for determining reflectivity of a therapeutic location on a retina during a laser shot (operation 704). The reflectivity may be determined, for example, based on the light reflected to an SLO, the greater the amount of light reflected indicating higher reflectivity. An SLO may be used, for instance, in conjunction with a therapeutic laser by being of a much lower power and in a separate wave band. Therapeutic retinal laser shots may take on the order of 100 ms. Thus, the determination may have to occur in a time frame less than this.

Process 700 also calls for adjusting the laser shot based on the reflectivity (operation 708). For example, a location having higher reflectivity may call for a more intense laser shot (e.g., increased power and/or pulse length), and a location having lower reflectivity may call for a weakened laser shot. The amount of reflectivity, which corresponds to the desire degree of retina whitening, at which to terminate the laser shot may be pre-set by the physician, for example. Process 700 is then at an end.

As will be appreciated by one skilled in the art, aspects of the present disclosure may be implemented as a system, method, or computer program product. Accordingly, aspects of the present disclosure may take the form of an entirely hardware environment, an entirely software embodiment (including firmware, resident software, micro-code, etc.), or an implementation combining software and hardware aspects that may all generally be referred to herein as a "circuit," "module," or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. In some instances, a computer readable storage medium may be, but is not limited to, an electronic, magnetic, optical, electromagnetic, infrared, or semiconductor system, apparatus, or device, or any suitable combination of the foregoing. More specific examples (a non-exhaustive list) of a computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be a tangible medium that can contain or store a program for use by or in connection with an instruction execution system, apparatus, or device.

A computer readable signal medium may include a propagated data signal with computer readable program code embodied therein, for example in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any medium, including but not limited to wireless, wireline, optical fiber cable, radio frequency (RF), etc., or any suitable combination of the foregoing.

Computer program code for carrying out operations for aspects of the disclosure may be written in any combination of one or more programming languages such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN), a wide area network (WAN), or a wireless network (e.g., Wi-Fi or cellular), or the connection may be made to an external computer (for example, through the Internet using an Internet Service Provider).

Aspects of the disclosure are described below with reference to flowchart illustrations and/or block diagrams of methods, apparatus (systems), and computer program products according to implementations. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other device to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus, or other devices to produce a computer implemented process such that the instructions that execute on the computer or other programmable apparatus provide processes for implementing the functions/acts specified in the flowchart and/or block diagram block or blocks.

Figure 8:
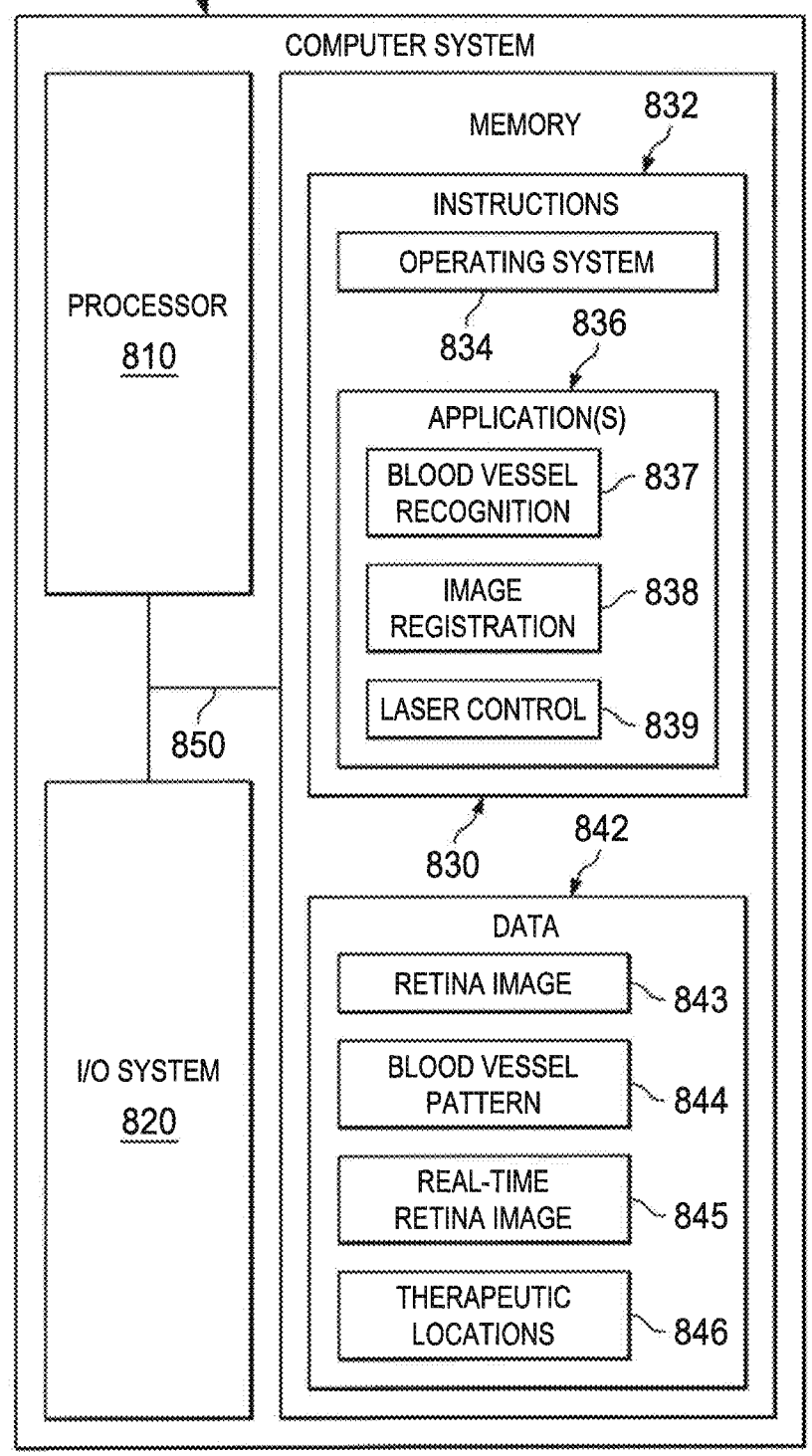
FIG. 8 is a Nock diagram illustrating an example computer system for retinal laser surgery.

FIG. 8 illustrates an example computer system 800 for retinal laser surgery. In some instances, system 800 may be part of a real-time fundus camera like real-time fundus camera 120. In other instances, however, the system 800 may be a separate system. In still other instances, the system 800 may form part of another component or device. System 800 includes a processor 810, an input/output system 820, and memory 830, which are coupled together by a network 850.

Processor 810 typically includes a logical processing unit (e.g., an arithmetic logic unit) that processes data under the direction of program instructions (e.g., from software). For example, processor 810 may be a microprocessor, a microcontroller, or an application specific integrated circuit. In general, the processor 810 may be any device that manipulates data in a logical manner.

Input/output system 820 may include, for example, one or more communication interfaces and/or one or more user interfaces. A communication interface may be, for instance, a network interface card (whether wireless or wireless) or a modem. A user interface could, for instance, be a user input device (e.g., a keyboard, a keypad, a touchpad, a stylus, or a microphone) or a user output device (e.g., a monitor, a display, or a speaker). In general, system 820 may be any combination of devices by Which a computer system can receive and output data.

Memory 830 may include, for example, random access memory (RAM), read-only memory (ROM), and/or disc memory. Various items may be stored in different portions of the memory at various times. Memory 830, in general, may be any combination of devices for storing data.

Memory 830 includes instructions 832 and data 842. Instructions 832 include an operating system 834 (e.g., Windows, Linux, or Unix) and applications 836. Data 842 includes the data required for and/or produced by applications 836.

In this implementation, applications 836 include blood vessel recognition 837, image registration 838, and laser control 839. Applications 837-839 may be separate applications or parts (e.g., subroutines or libraries) of a larger application. Data 842 includes a retina image 843, a blood vessel pattern 844, a real-time retina image 845, and therapeutic locations 846.

Network 850 is responsible for communicating data between processor 810, input/output system 820, and memory 830. Network 850 may include, for example, a number of different types of busses (e.g., serial and parallel).

In certain modes of operation, processor 810 processes retina image 843 according to blood vessel recognition application 837 to obtain blood vessel pattern 844. Retina image 843 may have been received through input/output system 820 from a fundus camera (e.g., diagnostic or real-time). Processor 810 then processes blood vessel pattern 844 and real-time retina image 845 according to registration application 838 to register blood vessel pattern 844 with real-time retina image 845.

Using laser control application 839, processor 810 may select a therapeutic location 846. In some instances, processor 810 may determine locations in need of therapy by identifying a predetermined location in need of therapy or determine locations based on an indication (e.g., user input) regarding a region in need of therapy. Processor 810 may determine one or more locations based on a region indication by taking into account a variety of factors (spot size, spot packing density, etc.).

Also according to laser control application 839, processor 810 determines whether the therapeutic location intersects with a blood vessel. If the therapeutic location intersects with a blood vessel, processor 810 may identify another location in need of therapy.

Once processor 810 identifies a location in need of therapy and not intersecting a blood vessel, processor 810 may instruct a beam guidance system to align a beam from a retinal laser with the location and instruct the retinal laser to fire when the beam guidance system has aligned the beam with the therapeutic location. The instructions may be sent using input/output system 820. After the retinal laser has fired, processor 810 may determine another appropriate therapeutic location, adjust the beam guidance system, and instruct the retinal laser to fire again.

In some modes of operation, computer system 800 may also perform other operations. For example, computer system 800 may command a retinal laser to adjust power (before or during a therapeutic laser shot) based on therapeutic location reflectivity. As another example, computer system 800 may register an updated retina image with blood vessel pattern 844 as a surgical procedure occurs.

The terminology used herein is for the purpose of describing particular implementations only and is not intended to be limiting. As used herein, the singular form "a", "an", and "the" are intended to include the plural forms as well, unless the context clearly indicates otherwise. It will be further understood that the terms "comprises" and/or "comprising," when used in the this specification, specify the presence of stated features, integers, steps, operations, elements, and/or components, but do not preclude the presence or addition of one or more other features, integers, steps, operations, elements, components, and/or groups therefore.

The corresponding structure, materials, acts, and equivalents of all means or steps plus function elements in the claims below are intended to include any structure, material, or act for performing the function in combination with other claimed elements as specifically claimed. The description of the present implementations has been presented for purposes of illustration and description, but is not intended to be exhaustive or limited to the implementations in the form disclosed. Many modifications and variations will be apparent to those of ordinary skill in the art without departing from the scope and spirit of the disclosure. The implementations were chosen and described in order to explain the principles of the disclosure and the practical application and to enable others or ordinary skill in the art to understand the disclosure for various implementations with various modifications as are suited to the particular use contemplated.

number of implementations have been described for retinal laser surgery, and several others have been mentioned or suggested. Moreover, those skilled in the art will readily recognize that a variety of additions, deletions, modifications, and substitutions may be made to these implementations while still performing retinal laser surgery. Thus, the scope of the protected subject matter should be judged based on the following claims, which may capture one or more concepts of one or more implementations.

What is claimed is:

1. A system comprising:
   an image processing subsystem to identify retina blood vessels in first image of a retina;
   a laser subsystem to apply a therapeutic shot to the retina;
   a laser control subsystem to determine a retina therapeutic location needing therapy, determine whether the therapeutic location substantially intersects an identified retina blood vessel, and if the therapeutic location substantially intersects an identified retina blood vessel, then determine a different therapeutic location that does not substantially intersect an identified retina blood vessel, the laser control subsystem configured to generate a command to activate the laser subsystem for the therapeutic location when a beam from the laser subsystem is aligned with the therapeutic location that does not substantially intersect an identified retina blood vessel; and an imaging subsystem to obtain a second image of the retina, wherein the second image of the retina is a real-time retina image;

wherein the image processing subsystem is configured to determine reflectivity of a retina location during a therapeutic laser shot;

wherein the laser control subsystem is configured to adjust the therapeutic laser shot based on the determined reflectivity and a variability limit established by a user for a laser setting; and wherein the image processing subsystem is configured to register the retina blood vessels of the second image with the retinal blood vessels of the first image.

2. The system of claim 1, further comprising an imaging subsystem to obtain the second image of the retina, wherein the second image of the retina is a real-time retina image, and wherein the real-time retina image is the retina image from which the retina blood vessels are identified.

3. The system of claim 1, further comprising a first imaging subsystem to obtain the first image of the retina.

4. The system of claim 3, further comprising a second imaging subsystem to obtain the second image of the retina.

5. The system of claim 3, wherein the first imaging subsystem comprises a scanning laser ophthalmoscope and the second imaging subsystem comprises a fundus camera.

6. The system of claim 3, wherein the image processing subsystem is configured to locate the retina blood vessels in the first image of the retina.

7. The system of claim 6, wherein the second imaging subsystem is configured to obtain a third image of the retina after one or more therapeutic laser shots; and the image processing subsystem is configured to register the retina blood vessels with the third image of the retina.

8. The system of claim 1, wherein the laser subsystem comprises a coagulation laser.

9. The system of claim 1, wherein:

the image processing subsystem is configured to determine reflectivity of a retina location needing therapy before application of a therapeutic laser shot; and the laser control subsystem is configured to adjust the laser shot based on the determined reflectivity.

10. The system of claim 1, further comprising a beam guidance subsystem to adjust the alignment of the beam from the laser subsystem.

11. The system of claim 10, wherein the beam guidance subsystem is controlled by the laser control subsystem.

12. The system of claim 11, wherein the beam guidance subsystem comprises a galvanometer mirror and associated drive.

13. The system of claim 10, wherein the beam guidance system comprises a rotatable glass prism.

14. The system of claim 1, wherein the system is configured to determine the reflectivity of the retina location using a scanning laser ophthalmoscope (SLO) at a lower power and a different wave band than the therapeutic laser shot.

15. A method comprising:

identifying retina blood vessels in an image of a retina;
determining a retina therapeutic location needing therapy;

determining whether the therapeutic location substantially intersects an identified retina blood vessel, and if the therapeutic location substantially intersects an identified retina blood vessel, then determine a different therapeutic location that does not substantially intersect an identified retina blood vessel;

generating a command to activate a retinal laser when a beam from the retinal laser is aligned with the therapeutic location that does not substantially intersect an identified retina blood vessel;

determining reflectivity of a retina location during a laser shot;

adjusting the laser shot based on the determined reflectivity and a variability limit established by a user for a laser setting;

obtaining the first image of the retina;
obtaining a second image of the retina; and
registering the retina blood vessels identified in the first image of the retina with the second image of the retina.

16. The method of claim 15, further comprising:
obtaining a third image of the retina after one or more therapeutic laser shots; and
registering the retina blood vessels with the third image of the retina.

17. The method of claim 15, further comprising:
determining reflectivity of a retina location needing therapy before application of a laser shot; and
adjusting the laser shot based on the determined reflectivity.

18. The method of claim 15, further comprising adjusting the alignment of the laser beam from the retinal laser.

19. The method of claim 15, further comprising generating a laser shot for the therapeutic location.

20. The method of claim 15, wherein second image is a real-time image of the retina.

21. The method of claim 15, further comprising:
obtaining a real-time image of the retina; and
registering the retina blood vessels with the real-time retina image.

22. The method of claim 15, wherein determining the reflectivity is done with a scanning laser ophthalmoscope (SLO) at a lower power and a different wave band than the laser shot.

23. A computer program product for retinal laser surgery, the computer program product comprising:

a non-transitory computer readable storage medium;
program instructions to identify retina blood vessels from a first retina image;
program instructions to determine a retina therapeutic location needing therapy;
program instructions to determine whether the therapeutic location substantially intersects an identified retina blood vessel, and if the therapeutic location substantially intersects an identified retina blood vessel, then determine a different therapeutic location that does not substantially intersect an identified retina blood vessel;
program instructions to generate a command to activate a retinal laser when a beam from the retinal laser will be aligned with the therapeutic location that does not substantially intersect an identified retina blood vessel;
program instructions to determine reflectivity of a retina location during a laser shot;
program instructions to adjust the laser shot based on the determined reflectivity and a variability limit established by a user for a laser setting;
program instructions to obtain a second retina image after one or more laser shots; and program instructions to register the retina blood vessels of the second retina image with the retina blood vessels of the first retina image;

wherein said program instructions are stored on said non-transitory computer readable storage medium.

24. The computer program product of claim 23, wherein the program instructions to identify retina blood vessels from the first retina image are adapted to identify the retina blood vessels from a real-time retina image.

25. The computer program product of claim 24, further comprising program instructions for obtaining the real-time image of the retina.

26. The computer program product of claim 23, further comprising program instructions to:

determine reflectivity of a retina location needing therapy before application of a laser shot; and adjust the laser shot based on the determined reflectivity.

27. The computer program product of claim 23, further comprising program instructions to adjust the alignment of the laser beam.

28. The computer program product of claim 23, wherein the reflectivity of the retina location is determined using a scanning laser ophthalmoscope (SLO) at a lower power and a different wave band than the therapeutic laser shot.

* * * * *